(12) United States Patent  
Kittrell

(10) Patent No.: US 7,019,541 B2  
(45) Date of Patent: Mar. 28, 2006

(54) ELECTRIC CONDUCTIVITY WATER PROBE

(75) Inventor: Michael E. Kittrell, Wichita, KS (US)

(73) Assignee: Crown Products, Inc., Wichita, KS (US)

( * ) Notice: Subject to any disclaimer, the term of this patent is extended or adjusted under 35 U.S.C. 154(b) by 0 days.

(21) Appl. No.: 10/846,910

(22) Filed: May 14, 2004

(65) Prior Publication Data

US 2005/0253601 A1    Nov. 17, 2005

(51) Int. Cl.
*G01R 27/08* (2006.01)

(52) U.S. Cl. .................. 324/696; 324/694; 73/863.71; 73/863.72; 73/863.73; 137/172; 137/625.47

(58) Field of Classification Search ............... 324/696, 324/694; 73/863.71, 863.72, 863.73; 137/172  
See application file for complete search history.

(56) References Cited

U.S. PATENT DOCUMENTS

| | | | |
|---|---|---|---|
| 2,295,097 A | 9/1942 | Waugh | |
| 3,088,592 A | 5/1963 | Clark | |
| 3,434,486 A | 3/1969 | Kasten | |
| 3,472,253 A | 10/1969 | Herscher | |
| 3,635,238 A | 1/1972 | Hankison et al. | |
| 3,721,265 A | 3/1973 | Hoffland | |
| 3,793,586 A * | 2/1974 | Heeps | 324/694 |
| 3,966,603 A | 6/1976 | Grant | |
| 4,103,700 A | 8/1978 | Orrell et al. | |
| 4,296,310 A * | 10/1981 | Luebke et al. | 219/440 |
| 4,328,825 A | 5/1982 | Bishai | |
| 4,491,143 A | 1/1985 | Yasuhara | |
| 4,585,022 A | 4/1986 | Haas et al. | |
| 4,799,504 A | 1/1989 | Scragg et al. | |
| 5,103,862 A | 4/1992 | McHugh | |
| 5,944,055 A | 8/1999 | Dicky | |
| 6,205,869 B1 * | 3/2001 | Schadt et al. | 73/863.71 |
| 6,675,834 B1 | 1/2004 | Lai | |

* cited by examiner

*Primary Examiner*—Anjan Deb  
*Assistant Examiner*—John Zhu  
(74) *Attorney, Agent, or Firm*—Kenneth H. Jack; Davis & Jack, L.L.C.

(57) ABSTRACT

An electric conductivity water probe consisting of a test chamber having a wall, a fluids input/output port, and a water input port, the wall having a first and at least a second wall section, the first and at least second wall sections being electrically isolated from each other by an electrical insulator; and a valve connected operatively to the fluids input/output port, the valve being adapted for alternately and permitting and resisting flows of fluids through the fluids port.

12 Claims, 5 Drawing Sheets

ELECTRIC CONDUCTIVITY WATER PROBE

FIELD OF THE INVENTION

The invention described hereinbelow relates to volatile fluids transport and storage systems. More particularly, said invention relates to such systems which incorporate structure adapted for separation of water from the volatile fluids, and which are adapted for collection of such water at a water collection point, said invention further relating to apparatus applicable to such water collection point and which are adapted for probing or testing for excessive water accumulations.

BACKGROUND OF THE INVENTION

An environment in which the instant inventive electric conductivity water probe may be advantageously used is an airport aircraft maintenance tarmac. In such environment, a fuel truck having a tank for transporting aircraft fuel commonly services aircrafts by pumping fuel into an aircraft's fuel tanks. Water, which upon occasion undesirably collects within and contaminates the tank of such a fuel truck, is necessarily prevented from being pumped into the aircraft's fuel tanks.

A common means for preventing water contaminated fuel from being pumped into an aircraft's fuel tanks is to interpose a water separating vessel or tank in line with a fuel transmission line extending between such truck and such aircraft. Such vessel commonly encases a first stage water coalescing element and a second stage water separating element, and has a fuel inlet port, a fuel outlet port, a low end water collecting sump, and a purging port for draining water from the sump.

In normal operation of such water separating vessels, only small amounts of water are expected to be separated from fuel which is pumped therethrough during a single aircraft refueling process. Such small volume of water is conveniently purged immediately following each aircraft fueling operation. However, on occasion, an excessive amount of water may be present within a fuel truck's tank, resulting in transmission of an excessive amounts of water to the water separating vessel. In the event water within the sump of such water separating vessel rises to a level at which portions of the vessel's coalescing and separating elements are submerged in water, the vessel's ability to further separate water from fuel may become compromised. Such a malfunction of the water separator potentially allows water laden fuel to be pumped into an aircraft's fuel tanks. In-flight aircraft engine failure and a catastrophic crash can result when the engine ingests water contaminated fuel.

In order to provide a safeguard against pumping water laden aircraft fuel downstream from a water separating vessel, means for detecting dangerously high water accumulations within such water separating vessels are commonly provided, such means operatively triggering, for example, a fuel truck pump motor "kill" switch. Electric conductivity water probes are a preferred means for detecting high water levels within such water separating vessels. Such probes desirably eliminate mechanical moving parts and avoid requirements of maintaining narrow buoyancy parameters which are inherent in fuel/water mechanical float switches.

Where an electric conductivity probe is utilized as a high water level testing means within such water separating vessel, the electrode or electric circuit completion point of such probe is typically mounted within or upon a wall of such water separating vessel in an orientation wherein the electrode is normally bathed and non-electrically conductive aircraft fuel. Under normal operating conditions, in the event that electrically conductive water rises within such water separating vessel to the level of such electrode, the aircraft fuel is washed away from the electrode by the water, and the water immediately completes an electric circuit which is communicated electrically for operation of, for example, a pump motor kill switch. However, aircraft fuel pumped through the water separator vessel may, on occasion, be further contaminated (over and above water contamination) by electrically insulating substances which tend to coat the electrode, acting as an electrical insulator. Where such electrode coating contaminants are present, excess water within the water separating vessel will not necessarily complete an electric circuit within the water probe. In such event, the aforementioned exemplary pump motor kill switch may not be actuated in response to an excess water event, and water laden fuel may be undesirably pumped downstream and into an aircraft's fuel tank.

A method for protecting against foreign matter deposit induced electric conductivity water probe failure is to shut down and disassemble the water separating vessel, exposing the interior electrical contact point or electrode to visual inspection. However, such measures are mechanically complex and time consuming, resulting in an undesirable aircraft refueling system down time.

Another known method of protecting against such foreign matter deposit induced electric conductivity water probe failure is to purposefully create high water conditions within the water separating vessel, and to observe the function of the water probe during the known high water event. However, such protective procedures similarly are time consuming, and undesirably result in aircraft fueling system down time.

The instant inventive electric conductivity water probe solves or ameliorates all of the problems set forth above by providing an electric conductivity water probe which is capable of normally functioning as a water test probe and which is further capable of alternately performing a function of "mimicking" a high water event within a water separating vessel without requiring the occurrence of an actual high water event.

BRIEF SUMMARY OF THE INVENTION

A major structural component of the instant invention comprises a walled electric conductivity water presence testing chamber having an interior space or bore. Said chamber necessarily has a fluids input/output port for facilitating an inward flow from a water separating vessel of, for example, normally present non-conductive jet fuel, and for alternately facilitating, in the event of high water within such vessel, simultaneous outwardly and inwardly crossing flows of the fuel and water.

First valve means are necessarily connected operatively to the fluids input/output port, said means being adapted for alternately permitting and resisting flows of fluids through the fluids input/output port. The first valve means may suitably comprise any of numerous commonly known "on/off" or "shutoff" flow controlling valves such as gate valves, ball valves, rotary spool valves, globe valves, angle valves, and the like. Preferably, the first valve means comprises a rotary spool or ball valve whose spool or ball includes a three port "T" channel, such valve performing functions (described below) over and above simply opening and closing the fluids input/output port. Preferably, an outer end of the test chamber's fluids input/output port comprises tank port mounting means allowing the fluids input/output port to be fixedly attached to, for example, the wall of a water collecting sump mounted at a low end of a jet fuel water separating vessel. Assuming that such sump has a helically threaded high water testing port, the tank port mounting means preferably comprises matching helical threads.

In addition to the above described fluids input/output port, the test chamber necessarily has a water input port situated inwardly from the first valve means. Said first valve means may be actuated to resist fluid flow through the fluids input/output port. Thereafter, electrically non-conductive jet fuel trapped within the test chamber may be purged, suitably by withdrawing the jet fuel through the water input port. More desirably, such fuel is purged through a separate fluids output port. Thereafter, the test chamber may be completely filled with a volume of electrically conductive water.

In order for electric conductivity water presence testing to be performed upon such volume of water, the wall of the test chamber preferably comprises a first wall section and at least a second wall section, the at least second section being electrically isolated or insulated from the first section. An electrical potential difference or voltage between the first and the at least second wall sections may be induced by allowing the first wall section to serve as an electrical ground, and by extending an electrically conductive lead wire outwardly from the at least second wall section to a voltage source. The volume of electrically conductive water which simultaneously bathes the first and at least second wall sections electrically bridges across the insulator and completes an electric circuit, facilitating passage of an electric current which may be communicated electrically for activation of, for example, a pump motor kill switch.

Like the fluids input/output port, the water input port is similarly preferably controlled by valve means, which may suitably comprise a separate gate valve, ball valve, rotary spool valve, globe valve, angle valve, removable plug, or removable cap. Notwithstanding, the water input port controlling valve means preferably comprises the same "T" ported rotary spool or ball valve which controls fluids flow through the fluids input/output port. Preferably, such shared valve member closes the water input port upon opening of the fluids input/output port, and alternately opens the water input port upon closure of the fluids input/output port.

Preferably, the electrically isolated at least second wall section comprises an electrode having a wire lead extending outwardly from an outer end, the electrode extending through a plastic sleeve insulator.

In operation of the instant inventive electric conductivity water probe, the fluids input/output port is normally open, the water input port is normally closed, and the fluids output port, if any, is normally closed. Assuming that an outer end of the fluids input/output port is connected to a high water level testing port of a water collection sump of a vessel adapted for separating water from fuel, such fuel normally flows through the fluids input/output port and normally fills the test chamber. Since aircraft fuel is normally electrically non-conductive, the fuel prevents the completion of an electric circuit between the electrically isolated first and at least second wall sections (e.g. between the typically metal wall casing of the test chamber and the insulated electrode extending through such wall). In the event that collected water rises within the water separating vessel to the level of the fluids input/output port, the water flows into the fluids input/output port while displacing and causing aircraft fuel within the test chamber to flow outwardly from the fluids input/output port, filling the test chamber with water. Since the water is normally electrically conductive, the water completes an electric circuit between the first and at least second wall sections of the test chamber.

A factor complicating the process described above results from further contamination of the fuel. Jet fuel potentially includes contaminants which are capable of coating the interior surfaces of the first and at least second wall sections of the test chamber, further electrically isolating those sections from each other. Where such surface coating contamination occurs, a high water event as described above may fill the test chamber with water without completing an electric circuit between the at least first and second wall sections. In such event, the electric conductivity water probe may undesirably fail to detect a high water event.

Periodic actuation of the instant invention's ability to "mimic" a high water event provides protections against undesirable high water detection failures as described above without requiring flooding of the water separating vessel with water. In order to cause the instant inventive electric conductivity water probe to mimic a high water event, the first valve means is actuated to close the fluids input/output port. Thereafter, fuel contained within the test chamber is purged, preferably by opening and reclosing a valve controlled fluids output port. Thereafter, the water input port is opened, and water is poured therethrough, filling the test chamber with electrically conductive water. In the event such water completes an electric circuit between the first and at least second wall sections of the test chamber, an operator may accurately infer that electric contact surfaces within such chamber have not been undesirably coated by any contaminants, and the operator may infer that the probe is properly functioning. Thereafter, the water may be purged through the fluids output port, and both the water input port and the fluids output port are thereafter closed. Thereafter, the fluids input/output port is reopened, restoring the test probe to normal water level testing function.

Accordingly, an object of the instant invention is to provide an electric conductivity water probe which incorporates structural features, adapting the probe for periodically "mimicking" a high water event, such probe providing assurances, over time, of the probe's electrical testing integrity.

Other and further objects, benefits, and advantages of the instant invention have been described above, and further appear in the Detailed Description and drawings which follow.

DETAILED DESCRIPTION OF A PREFERRED EMBODIMENT

Figure 1:
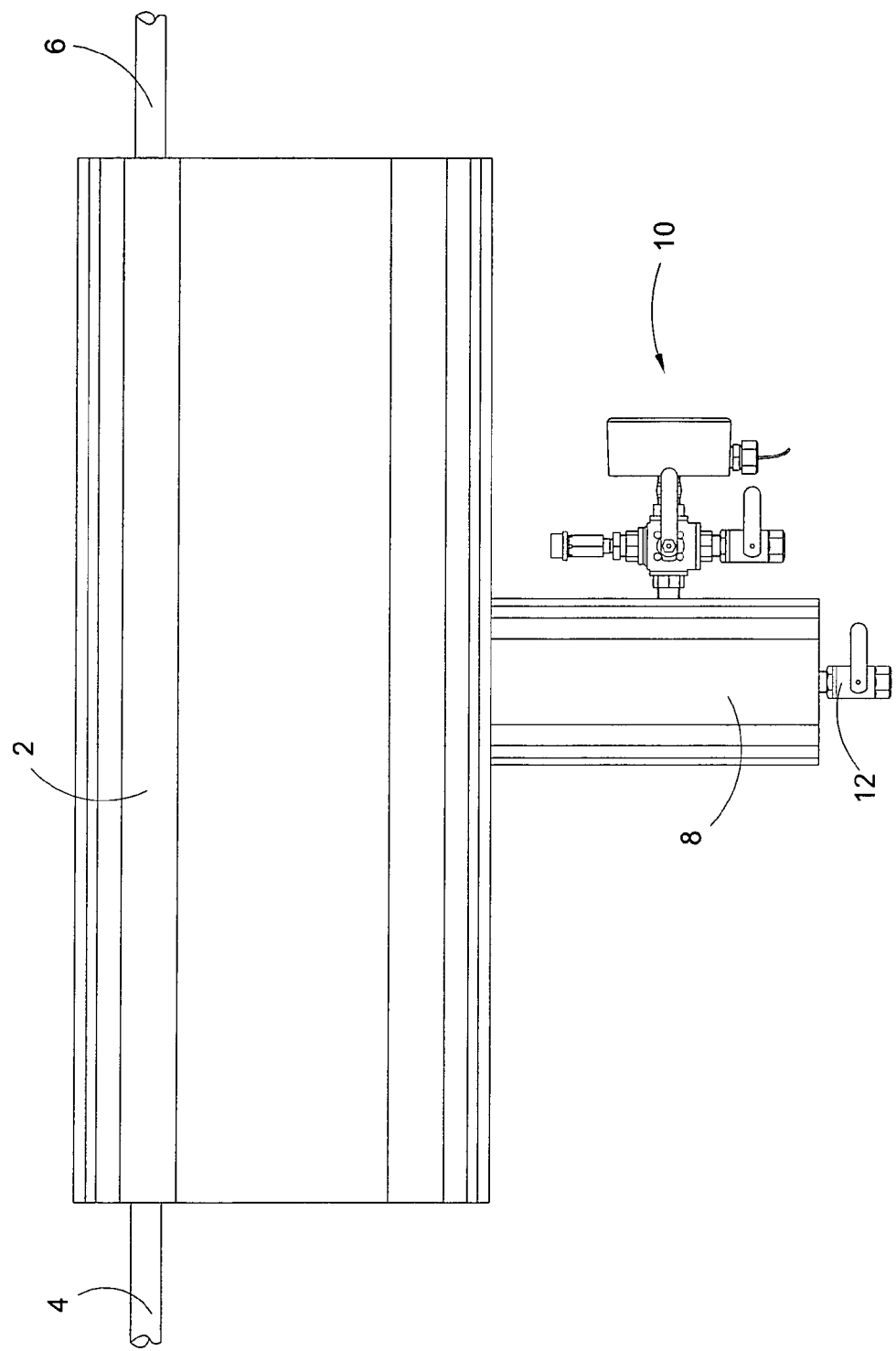
FIG. 1 depicts the instant inventive electric conductivity water probe 10, the view showing the probe mounted, for the sake of example, upon a water separating vessel 2 having a water collecting sump 8.
Figure 2:
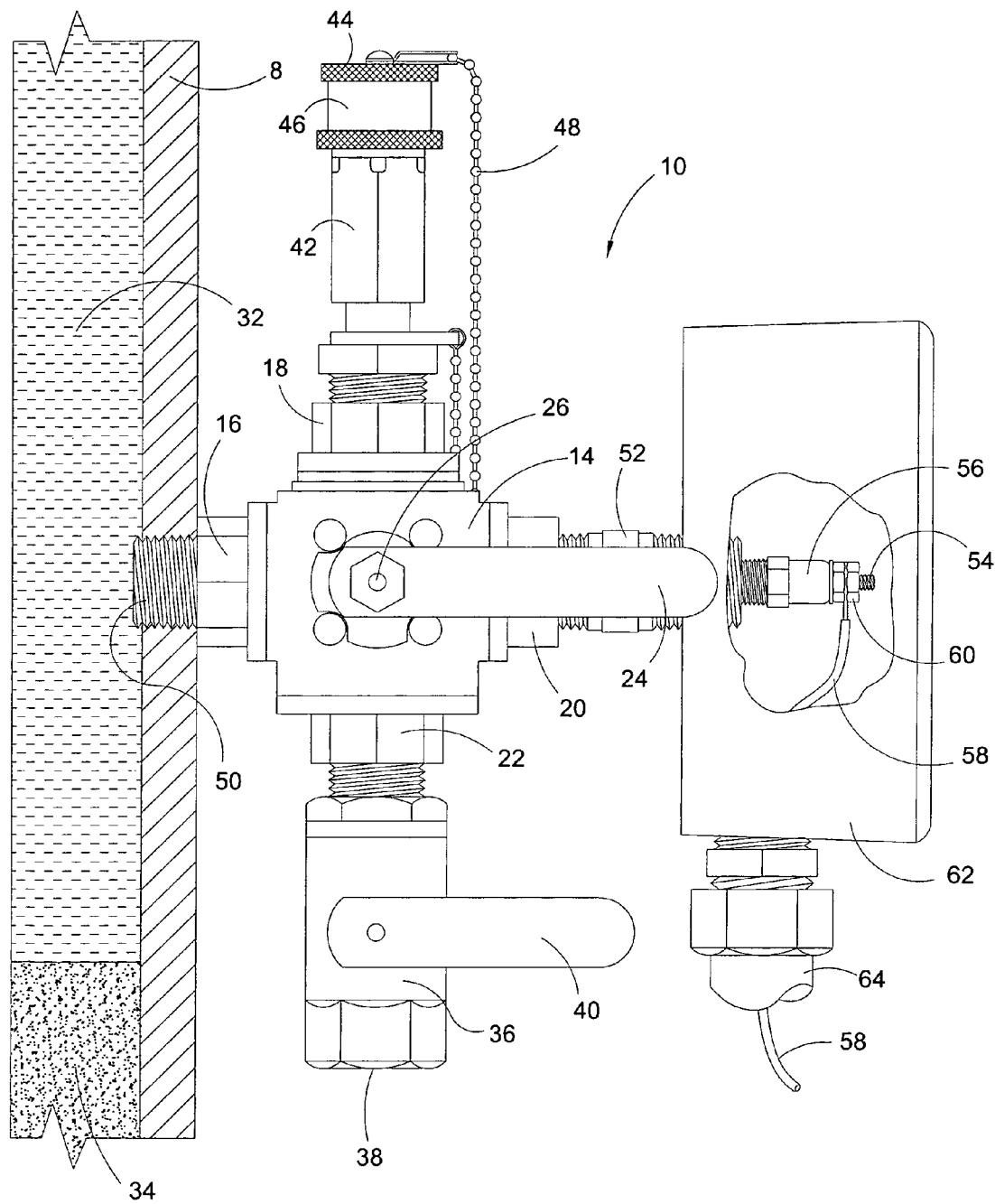
FIG. 2 is a magnified view of the probe of FIG. 1, the view showing in cutaway a portion of the sump 8.

Referring now to the drawings, and in particular to FIG. 1, the instant inventive electric conductivity water probe is referred to generally by Reference Arrow 10. The electric conductivity water probe 10 is shown attached to a water collecting sump 8, such sump being attached at a low end of, for example, an aircraft fuel water separating vessel 2. Aircraft fuel may be pumped from a fuel truck (not depicted) through fuel line 4 and into separating vessel 2. Thereafter, water coalescing and water separating elements (not depicted) encased within vessel 2 separate water from the fuel. De-watered fuel emits from fuel line 6 for transmission to, for example, an aircraft's fuel tank (not depicted). Water separated within vessel 2 flows downwardly into water collecting sump 8. Under normal circumstances, such collected water does not rise within sump 8 above the level of probe 10. After each fueling operation, water purge valve 12 may be opened, allowing collected water from to drain from sump 8. Referring further to FIG. 2, in the event that collected water within sump 8 rises to the level of the fluids input/output port 16 of probe 10, probe 10 functions to trigger cessation of fuel transmission as described below.

Figure 3:
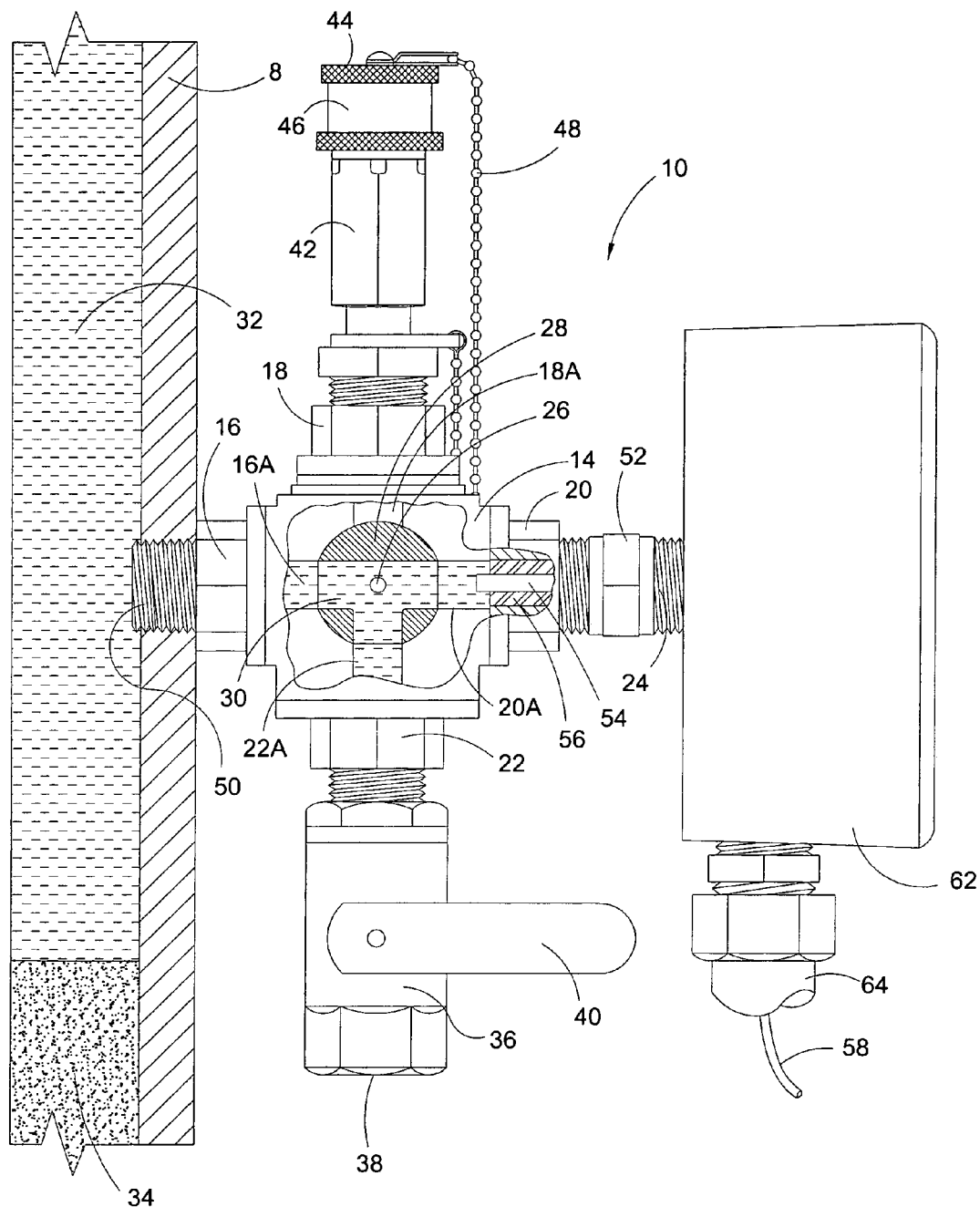
FIG. 3 redepicts FIG. 2, the view of FIG. 3 showing a cutaway portion of a side wall of the main rotary valve component of the probe 10.

Referring simultaneously to FIGS. 2 and 3, the electric conductivity water probe 10 preferably comprises a four port "+" configured valve casing 14, such casing having an internal valve spool or valve ball 28 mounted rotatably upon axle 26. The valve casing 14 has a fluids input/output port 16, a water input port 18, an electrode mounting port 20, and a fluids output port 22. Channels 16A, 18A, 20A, and 22A extending in the "+" configuration through valve casing 14 along with "T" channel 30 extending through spool or ball 28 define an electric conductivity test chamber, and provide fluid communication between ports 16, 18, 20, and 22.

Referring further simultaneously to FIGS. 2 and 3, the outer end of fluids input/output port 16 preferably has helical threads 50 for helically threaded mounting upon sump 8 at a desired high water testing level.

Referring further simultaneously to FIGS. 2 and 3, outward flow of fluids from the fluids output port 22 is preferably controlled by a ball valve which is manually openable and closable by turn handle 40.

Figure 4:
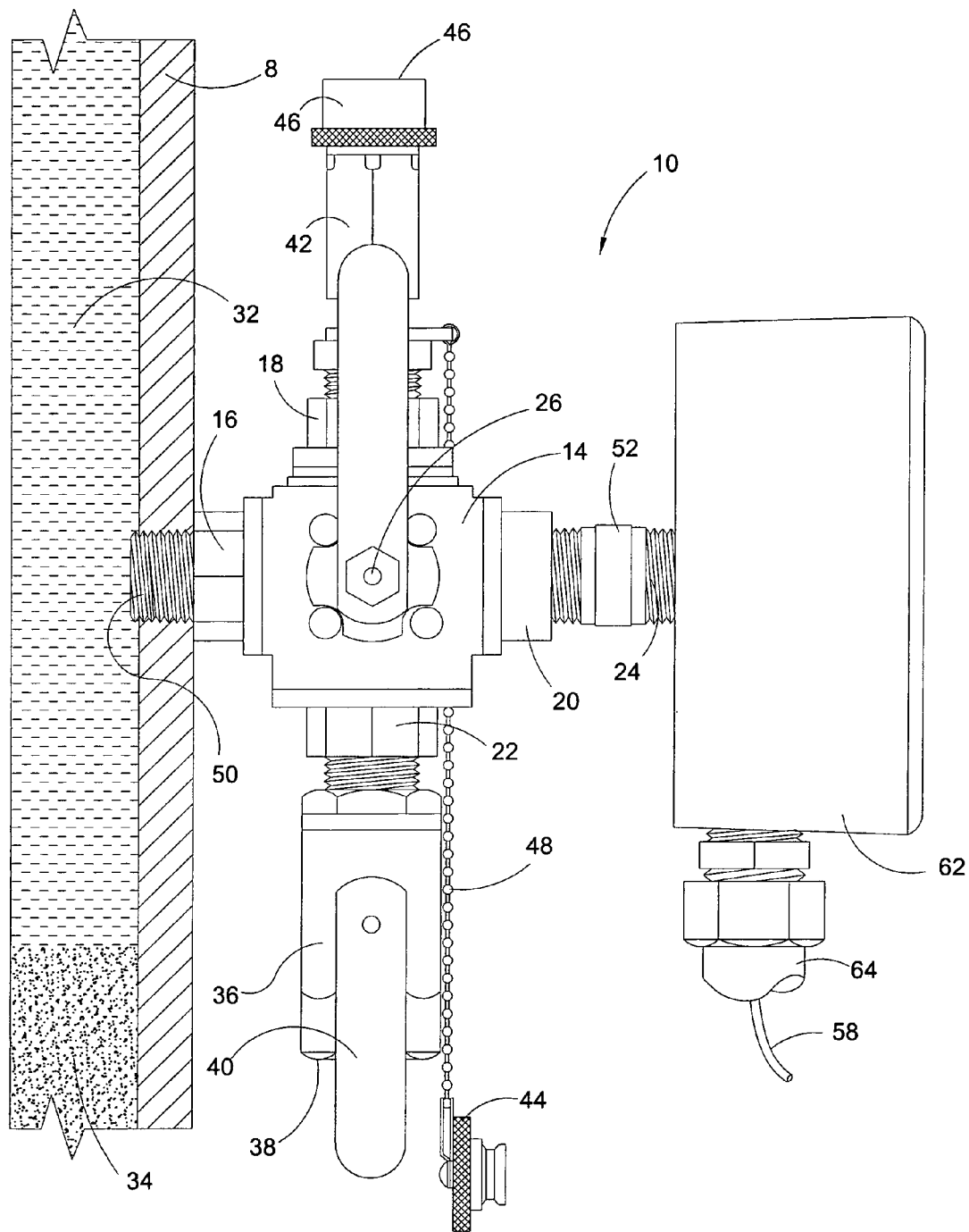
FIG. 4 redepicts FIG. 2 showing valves alternately oriented.
Figure 5:
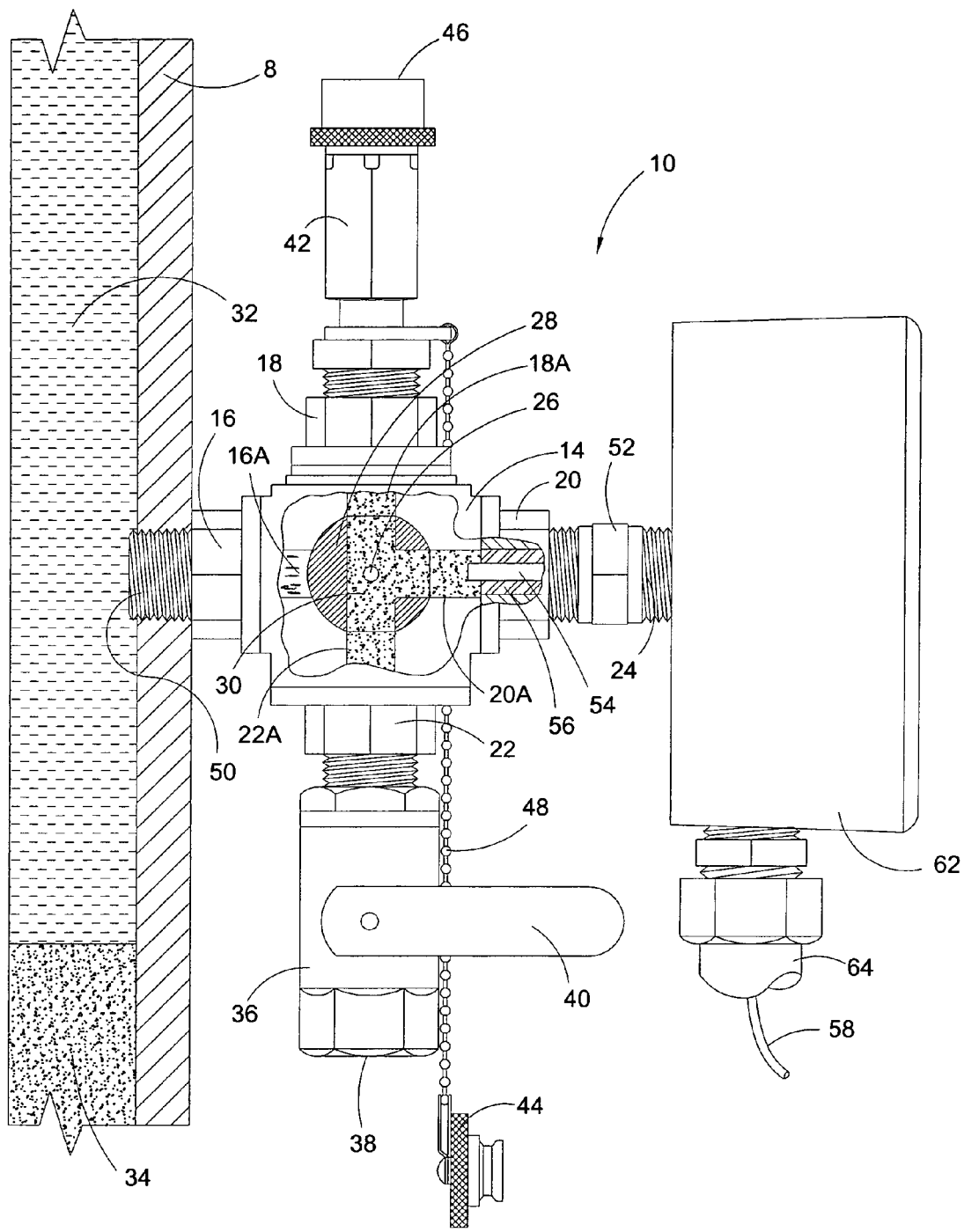
FIG. 5 redepicts FIG. 3 showing valves alternately oriented.

Referring further simultaneously to FIGS. 2 and 3, flows of fluids into and out of the water input port 18 is preferably controlled (in addition to the operation of rotary element 28) by a quick disconnect coupling Shrader valve 42, such valve having a quick disconnect sleeve 46, and, referring further simultaneously to FIG. 4, having a quick disconnect plug 44. In order to inject water into and through water input port 18, coupling sleeve 46 is slidably moved downwardly and plug 44 is withdrawn from the position depicted in FIG. 3 and is allowed to hang upon chain 48 in the position depicted in FIG. 4. Thereafter, a funnel (not depicted) having a nipple configured similarly with plug 44 and fitted for downward extension into opening 46 actuates and opens the Shrader valve 42, permitting downward flow of electrically conductive water through water input port 18. Suitably, a lever operated ball valve similar to ball valve 36 may be substituted for the quick disconnect coupling Shrader value 42.

Referring to FIG. 3, the electrode mounting port 20 threadedly receives a hollow bored and helically threaded junction box coupler 52. A plastic insulating sleeve 56 is nestingly received within the bore of coupler 52, and an electrically conductive metal electrode 54 is concentrically nestingly received within the bore of insulating sleeve 56. The electrode 54 so situated constitutes a section of the wall of the electric conductivity test chamber, such wall section being electrically isolated from other sections of such wall via the sleeve insulator 56. Preferably, all components depicted in FIG. 3 other than insulator 56 comprise electrically conductive metal, providing for electrical grounding of electrode 56 upon electrical bridging via water contacts across the inner end of the insulator 56.

Referring simultaneously to FIGS. 2 and 3, an electric junction box 62 is preferably threadedly mounted upon helical threads 24 of coupler 52. Also, preferably, outer ends of the electrical insulator 56 and the electrode 54 are exposed within the interior of junction box 52 for attachment of an electric lead wire 58 by threaded nut attachments 60. Preferably, protective electrical conduit 64 extends downwardly from junction box 62, the lead wire 58 being protected by such conduit.

In operation of the instant inventive electric conductivity water probe 10, referring simultaneously to FIGS. 1–3, valve handle 24 is normally oriented as depicted in FIG. 2, such handle position orienting "T" channel 30 as depicted in FIG. 3. At such valve setting, "T" channel 30 provides fluid communication between fluids input/output port 16, the inner end of electrode 54, and between the water output port 22. Also, at such setting, the rotary spool or ball 28 simultaneously closes the water input port 18. Also, at such setting, channels 16A, 20A, 22A, and 30 define an electric conductivity test chamber.

During normal operations referring further to FIGS. 1–3, water 34 collected within water sump 8 fills only to a point underlying the fluids input/output port 16. In such circumstances, after completion of a fueling operation, water purging valve 12 may be opened allowing water 34 to downwardly emit therefrom until a flow of normally differently colored fuel 32 is visibly confirmed. Thereafter, valve 12 is closed and the system is readied for a next fueling operation.

Referring further simultaneously to FIGS. 1–3, in the event that collected water 34 rises to the level of fluids input/output port 16, such water 34, being heavier than fuel 32, flows into fluids input/output port 16, and displaces the fuel 32 from channels 16A, 20A, 22A, and 30, causing the fuel to simultaneously flow outwardly from the fluids input/output port 16. Upon complete displacement of such fuel by the water, the water normally completes an electric circuit between the preferably metallic valve casing 14 and the electrode 54, initiating an electric current or measurable amperage within lead wire 58. Preferably, such electric current is conveyed as a pilot signal for control of a pump motor kill switch, terminating fuel pumping in response to the high water event.

Referring further simultaneously to FIGS. 1–3, long exposure of the surfaces of channel 28A and the inward surfaces of electrode 54 to fuel 32 may allow contaminants within fuel 32 to coat and insulate such surfaces. Upon such undesirable surfaces coating, the occurrence of a high water event such as described above, may fail to result in a completion of an electric circuit between the valve casing 14 and the electrode 54, such failure preventing the transmission of a kill switch actuating signal via wire 58 upon occurrence of a high water event.

In order to guard against and prevent the occurrence of a water presence testing failure such as described above, the electric conductivity water probe 10 may be periodically operated to "mimic" a high water event. Mimicking a high water event desirably reproduces high water conditions within a water separator (see FIG. 1) without water flooding a major component of a refueling system. Referring to FIGS. 2–5, the high water mimicking process commences by turning handle 24 counter-clockwise ninety degrees from the position depicted in FIG. 2 to the position depicted in FIG. 4. Such handle manipulation rotates spool or ball 28 counter-clockwise ninety degrees, reorienting "T" channel 30 from the position depicted in FIG. 3 to the position depicted in FIG. 5. Upon such rotation, Shrader valve 42 and ball valve 36 prevent fuel 32 which is trapped under pressure within "T" channel 30 from spraying upwardly and downwardly from probe 10. Upon rotation of handle 24 and of spool or ball 28 counterclockwise ninety degrees, as described above, ball valve 36 is opened by turning handle 40 clockwise ninety degrees from the position of FIG. 2 to the position of FIG. 4. Upon opening of valve 36, fuel 32 contained within "T" channel 30 purges downwardly from valve opening 38. Thereafter, handle 40 is turned counter-clockwise from the position depicted in FIG. 4 to the position in FIG. 5, reclosing valve 36. Thereafter, electrically conductive water is poured into the upper opening 46 of Shrader valve 42 in the manner described above, filling "T" channel 30 and channel 20A with water represented by dotted hatching. Thereafter, an electrical potential difference between lead wire 58 and metal valve casing 14 is established, and the assembly is electrically tested for existence of electric current within lead wire 58. A presence amperage within lead wire 58 indicates that the water within "T" channel 30 and within channel 20A has electrically bridged the inner end of insulator 56, and confirms that a contaminating electrically insulating coating is not present at the inner ends of insulator 56 and electrode 54. In the event that such electric bridging is not detected, the electric conductivity probe 10 is normally disassembled for internal cleaning and maintenance.

Referring simultaneously to all figures, reversal of steps described above purges water from "T" channel 30 and restores the electric conductivity water probe 10 to its normal operating configuration as depicted in FIGS. 1, 2, and 3.

While the principles of the invention have been made clear in the above illustrative embodiment, those skilled in the art may make modifications in the structure, arrangement, portions and components of the invention without departing from those principles. Accordingly, it is intended that the description and drawings be interpreted as illustrative and not in the limiting sense, and that the invention be given a scope commensurate with the appended claims.

I claim:

1. An electric conductivity water probe comprising:
 (a) a water presence testing chamber having a wall, the wall having a fluids input/output port and a water input port, the wall further having a first and at least a second wall section;
 (b) electrical insulating means interposed between the first and at least second wall sections; and
 (c) first valve means connected operatively to the fluids input/output port, the first valve means being adapted for alternately permitting and resisting flows of fluids through the fluids input/output port.

2. The electric conductivity water probe of claim 1 wherein the at least second wall section comprises an electrode.

3. The electric conductivity water probe of claim 2 wherein the water presence testing chamber further has a fluids output port.

4. The electric conductivity water probe of claim 3 wherein the first valve means is further adapted for, upon permitting flows of fluids through the fluids input/output port, resisting flows of fluids through the water input port.

5. The electric conductivity water probe of claim 4 further comprising second valve means connected operatively to the fluids output port, the second valve means being adapted for alternately permitting and resisting flows of fluids through the fluids output port.

6. The electric conductivity water probe of claim 5 wherein the first valve means comprises a three port rotary valve spool or a three port rotary valve ball, and wherein the water presence testing chamber comprises a valve casing, said spool or ball being rotatably mounted within the valve casing.

7. The electric conductivity water probe of claim 6 wherein the second valve means comprises a valve selected from the group consisting of Shrader valves, gate valves, ball valves, rotary spool valves, globe valves, angle valves, removable caps, removable plugs, and pinch valves.

8. The electric conductivity water probe of claim 7 further comprising third valve means connected operatively to the water input port, the third valve means being adapted for alternately permitting and further resisting flows of fluids through the water input port.

9. The electric conductivity water probe of claim 8 wherein the third valve means comprises a valve selected from the group consisting of Shrader valves, gate valves, ball valves, rotary spool valves, globe valves, angle valves, removable caps, removable plugs, and pinch valves.

10. The electric conductivity water probe of claim 2 wherein the first wall section comprises metal, and wherein the electrical insulating means comprises a sleeve insulator, the electrode being received nestingly by the sleeve insulator.

11. The electric conductivity water probe of claim 10 wherein the electrode has inner and outer ends and further comprising an electric lead wire connected electrically to the outer end of the electrode.

12. The electric conductivity water probe of claim 11 wherein the fluids input/output port has an outer end, and further comprising tank port mounting means fixedly attached to or formed wholly with the outer end of the fluids input/output port.

* * * * *